United States Patent
Deshpande et al.

(10) Patent No.: US 7,683,205 B2
(45) Date of Patent: Mar. 23, 2010

(54) PROCESS FOR THE PREPARATION OF RIVASTIGMINE

(75) Inventors: Pandurang Balwant Deshpande, Vadodara (IN); Kishore Khemani, Vadodara (IN); Bharat Becharbhai Boda, Vadodara (IN); Tushar Rajnikant Shah, Vadodara (IN); Hitarth Harshendu Acharya, Vadodara (IN); Parven Kumar Luthra, Vadodara (IN)

(73) Assignee: Alembic Limited, Gujarat (IN)

( * ) Notice: Subject to any disclaimer, the term of this patent is extended or adjusted under 35 U.S.C. 154(b) by 566 days.

(21) Appl. No.: 11/590,566

(22) Filed: Oct. 31, 2006

(65) Prior Publication Data

US 2008/0045743 A1 Feb. 21, 2008

(30) Foreign Application Priority Data

Aug. 17, 2006 (IN) .................. 1290/MUM/2006

(51) Int. Cl.
*C07C 271/40* (2006.01)
*C07C 215/46* (2006.01)
(52) U.S. Cl. .................. 560/136; 560/132; 564/390
(58) Field of Classification Search ............. 560/136, 560/132; 564/390
See application file for complete search history.

(56) References Cited

U.S. PATENT DOCUMENTS

| 4,948,807 A | 8/1990 | Rosin et al. |
| 5,602,176 A | 2/1997 | Enz |

FOREIGN PATENT DOCUMENTS

| WO | WO 03/101917 | 12/2003 |
| WO | WO 2004/037771 | 5/2004 |
| WO | WO 2006048720 A1 * | 5/2006 |
| WO | WO 2006/068386 | 6/2006 |

* cited by examiner

*Primary Examiner*—Rebecca L Anderson
*Assistant Examiner*—Jason Nolan
(74) *Attorney, Agent, or Firm*—Hamre, Schumann, Mueller & Larson, P.C.

(57) ABSTRACT

The present invention relates to an improved process for preparation of Rivastigmine of formula (I) or pharmaceutically acceptable salts thereof comprising a step of N-methylation of compound of formula (III), wherein $R_1=R_2=H$ or $R_1=H$ and $R_2=CH_3$ or an acid addition salt thereof, using paraformaldehyde in the presence of Raney Nickel and hydrogen in a suitable solvent to obtain compound of formula (II).

10 Claims, 1 Drawing Sheet

PROCESS FOR THE PREPARATION OF RIVASTIGMINE

FIELD OF INVENTION

The present invention relates to an improved process for the preparation of Ethylmethylcarbamic acid 3-[(1S)-1-(dimethylamino) ethyl]phenyl ester of formula (I) or pharmaceutically acceptable salts thereof, commonly known as Rivastigmine.

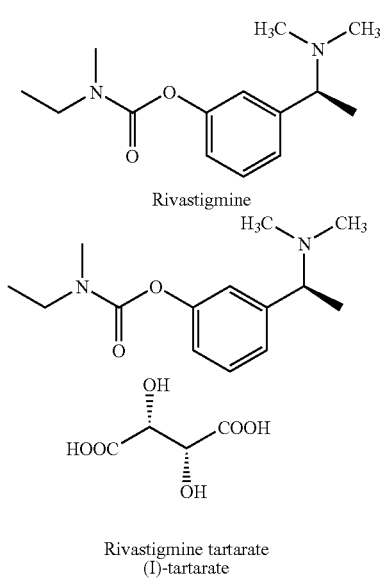

Rivastigmine

Rivastigmine tartarate
(I)-tartarate

BACKGROUND OF THE INVENTION

Rivastigmine is prescribed for the treatment of mild to moderate Alzheimer's disease. The tartarate salt of Rivastigmine is marketed under brand name of Exelon®. Rivastigmine is in a class of medications called cholinesterase inhibitors. It improves mental function by increasing the amount of a certain natural substance in the brain. Rivastigmine increases the amounts of a chemical called acetylcholine in the brain. Acetylcholine may be involved in memory, attention, and learning.

U.S. Pat. No. 4,948,807 describes process for preparation of racemic Rivastigmine by reacting α-m-hydroxyphenylisopropyldimethylmine or α-m-hydroxyphenyl ethyldimethylmine with carbomyl chloride in the presence of NaH. Process for resolution of racemic Rivastigmine is described in U.S. Pat. No. 5,602,176, which involves resolution using di-o,o'-p-toluoyl tartaric acid. The major drawback of this process is repeated recrystallization in the final step to achieve increased enantiomeric excess, which results in decreased yield with increase in processing steps.

PCT publication no. WO03/101917 describes process for preparation of Rivastigmine by condensing N-ethyl-N-methyl-4-nitrophenyl carbamate, which is obtained from 4-nitrophenyl chloroformate, with [1-(3-hydroxyphenyl) ethyl] dimethylamine, which is obtained by demethylation of [1-(3-methoxyphenyl) ethyl]dimethylamine, in the presence of base. The process of preparation of [1-(3-hydroxyphenyl) ethyl]dimethylamine involves use of DL-methionine and 50% sulphuric acid. DL-methionine is a costly reagent and also a skin, eye and respiratory irritant The process described in PCT publication no. WO2004/037771 involves reductive amination of 3-methoxy acetophenone in presence of dimethylamine, titanium isopropoxide and sodium borohydride to obtain [1-(3-methoxyphenyl) ethyl]dimethylamine, which is further demethylated using hydrobromic acid to obtain 3-(1-dimethylamino)phenol. This is further resolved using (S)-(+)-camphor-10-sulfonic acid and reacted with carbamoyl chloride to obtain Rivastigmine. Titanium isopropoxide and sodium borohydride are very expensive reagents which lead to increase in overall cost of the process. Moreover hydrobromic acid is hazardous in nature and thus making it difficult to handle at commercial scale.

The process for preparation of 3-(1-dimethylamino)phenol as described in PCT publication no. WO2006/068386 involves subjecting (S)-3-(1-dimethylaminoethyl)phenol to N-methylation using formaldehyde/formic acid. Further it is subjected to O-carbamoylation to obtain Rivastigmine. It was observed by the inventors of present invention that by process described here, the product obtained did not have desired physical properties and the yield of reaction was also poor.

Therefore there is a need to develop a process for preparation for preparation of Rivastigimine and its intermediates which is simple, cost effective, non-hazardous and commercially viable.

OBJECT OF THE INVENTION

Therefore it is an object of the present invention to provide a process for the preparation of Rivastigmine of formula (I) or pharmaceutical acceptable salts thereof and its intermediates.

Yet another object of the present invention is to provide a process for the preparation of Rivastigmine of formula (I) or pharmaceutical acceptable salts thereof and its intermediates which is high yielding and has short reaction times.

Further object of the present invention is to provide a process for the preparation of Rivastigmine of formula (I) or pharmaceutical acceptable salts thereof and its intermediates which is simple, cost effective, nonhazardous and commercially viable.

SUMMARY OF THE INVENTION

In accordance with the object of the present invention, one aspect provides a process for the preparation of Rivastigmine of formula (I) or pharmaceutically acceptable salts thereof, comprising a step of N-methylation of compound of formula (III), wherein $R_1=R_2=H$ or $R_1=H$ and $R_2=CH_3$ or an acid addition salt thereof, using paraformaldehyde in the presence of Raney Nickel and hydrogen in a suitable solvent to obtain compound of formula (II)

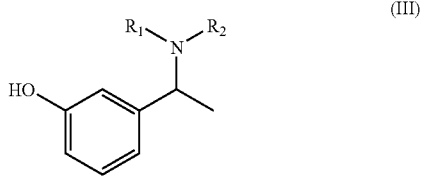

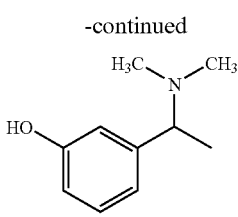

Another object of the present invention, one aspect provides a process for the preparation of Rivastigmine of formula (I) or pharmaceutically acceptable salts thereof, comprising steps of,
(a) N-methylation of compound of formula (III), wherein $R_1=R_2=H$ or $R_1=H$ and $R_2=CH_3$ or an acid addition salt thereof, using paraformaldehyde in the presence of Raney Nickel and hydrogen in a suitable solvent to obtain compound of formula (II)

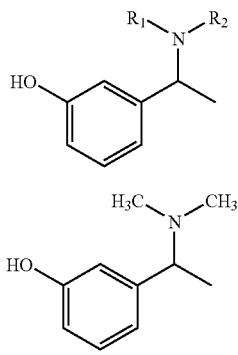

(b) optically resolving compound of formula (II) to obtain desired isomer (II')

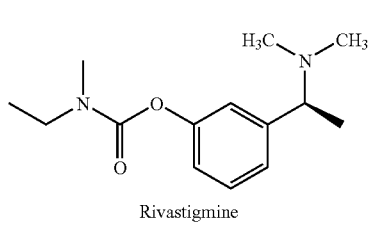

(c) converting compound of formula (II') to Rivastigmine of formula (I) and optionally converting it to pharmaceutically acceptable salts thereof Rivastigmine Yet another aspect of the present invention provides a process for preparation of compound of formula (II) comprising of N-methylation of compound of formula (III), wherein $R_1=R_2=H$ or $R_1=H$ and $R_2=CH_3$ or an acid addition salt thereof, using paraformaldehyde in the presence of Raney Nickel and hydrogen in a suitable solvent.

Further aspect of the present invention provides process for preparation of Rivastigmine or pharmaceutically acceptable salts thereof, and its intermediates which is simple, non-hazardous, high yielding, results in lesser amount of impurities, has shorter reaction duration, and is economic and commercially viable.

DETAIL DESCRIPTION OF THE INVENTION

Figure 1:
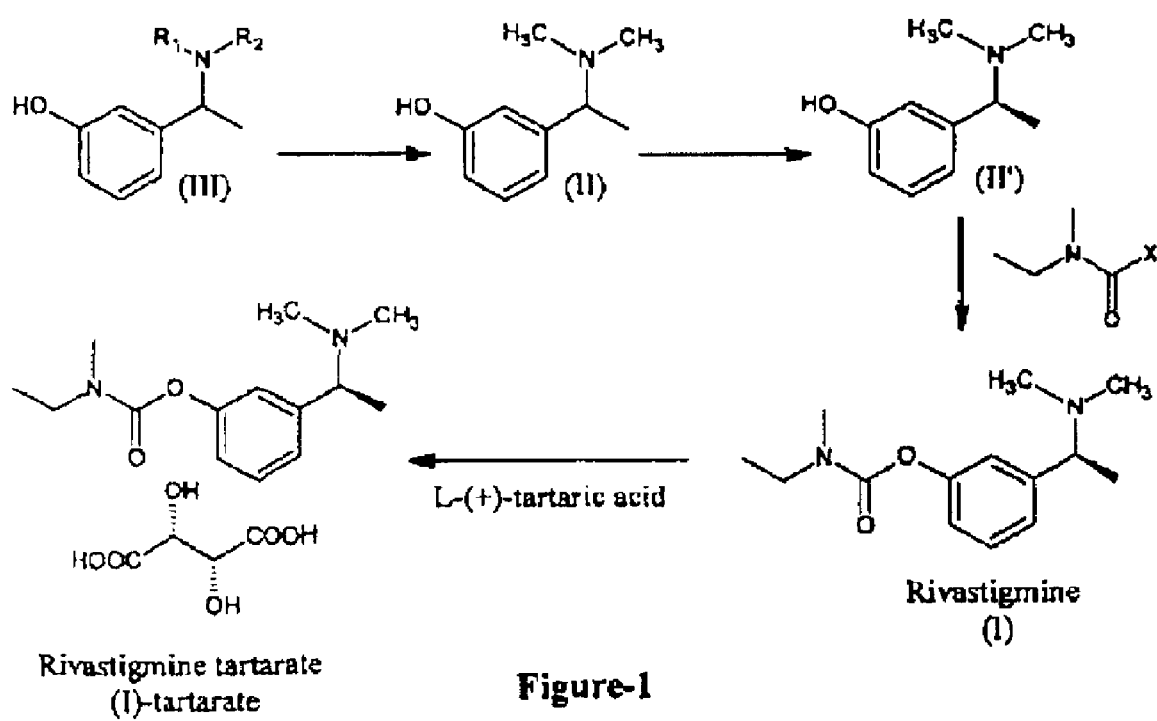
FIG. 1 illustrates a process for preparation of Rivastigmine.

The present invention provides process for preparation of Rivastigmine of formula (I) or pharmaceutically acceptable salts thereof and its intermediates by process shown in FIG. 1.

In accordance with the object of the present invention one of the preferred embodiment provides process for the preparation of Rivastigmine or pharmaceutically acceptable salts thereof, comprising a step of N-methylation of compound of formula (III), wherein $R_1=R_2=H$ or $R_1=H$ and $R_2=CH_3$ or an acid addition salt thereof, using paraformaldehyde in the presence of Raney Nickel and hydrogen in a suitable solvent to obtain compound of formula (II)

The N-methylation of compound of formula (III) is carried out using paraformaldehyde in the presence of Raney Nickel and hydrogen in a suitable solvent. Suitable solvent can be selected from group comprising of alcohols, esters, chlorinated hydrocarbons or mixtures thereof, examples of which include but are not limited to methanol, ethanol, isopropanol, ethylacetate, methylacetate, butylacetate, chloroform, methylene dichloride, ethylene dichloride and the like or mixtures thereof.

The reaction is carried out at temperature range of about ambient temperature to about reflux temperature of the solvent, more preferably at 25° C. to 80° C. The duration of the reaction is about 2 hours to about 10 hours, preferably 3 hours to 6 hours. The hydrogen pressure is maintained between 5 kg/cm² and 15 kg/cm², preferably 10 kg/cm².

After completion of the reaction the product is isolated by normal work up procedures. The crude product thus obtained can be further purified by crystallization from solvent selected from aromatic hydrocarbons, ethers or mixtures thereof for example toluene, petroleum ether and the like or mixtures thereof. Compound of formula (II) obtained by the process of present invention has purity greater than about 95%, preferably 97% and more preferably 98%. The yield of reaction is greater than about 80%, preferably 83% and more preferably 85%.

Another preferred embodiment of the present invention provides process for the preparation of Rivastigmine or pharmaceutically acceptable salts thereof, comprising steps of,
(a) N-methylation of compound of formula (III), wherein $R_1=R_2=H$ or $R_1=H$ and $R_2=CH_3$ or an acid addition salt thereof, using paraformaldehyde in the presence of Raney Nickel and hydrogen in a suitable solvent to obtain compound of formula (II)
(b) optically resolving compound of formula (II) to obtain desired isomer (II')
(c) converting compound of formula (II') to Rivastigmine of formula (I) and optionally converting it to pharmaceutically acceptable salts thereof.

Yet another embodiment of the present invention provides process for preparation of compound of formula (II) comprising of N-methylation of compound of formula (III), wherein $R_1=R_2=H$ or $R_1=H$ and $R_2=CH_3$ or an acid addition salt thereof, using paraformaldehyde in the presence of Raney Nickel and hydrogen in a suitable solvent.

Compound of formula (III) is prepared by reductive amination of 3-hydroxy acetophenone in the presence of methyl amine.

The compound of formula (II) thus obtained can be further resolved by process known perse or by any method known to person skilled in art. Preferably compound of formula (II) is resolved using d-camphorsulphonic acid in ethanol to obtain desired isomer of formula (II'). Compound of formula (II') is converted to Rivastigmine or a pharmaceutically acceptable salt thereof by methods know to person skilled in art or any method well-known in the prior art.

In a preferred embodiment compound of formula (II') is further subjected to O-carbamoylation in the presence of base to obtain Rivastigmine of formula (I). Rivastigmine can be optionally converted to desired pharmaceutically acceptable salt, preferably tartarate salt by conventional methods.

The process of the present invention is illustrated by the following examples and should not be construed so as to limit the scope of the invention in any manner.

EXAMPLES

Example 1

Preparation of α-m-hydroxy phenylethyldimethylamine

N-methylation was carried out on α-m-hydroxy phenylethylamine (25 g) with Paraformaldehyde (33 g) in presence of Raney Nickel (30 g) in methanol (500 ml) at 80° C. and 10 kg/cm$^2$ of hydrogen pressure in an autoclave. After 3-4 hours the product was isolated by removing Raney nickel and concentrating the filtrate. The product was further purified by dissolving the crude product in Toluene (50 ml) and is crystallized by slow addition of Petroleum ether (150 ml). Pure α-m-hydroxy phenylethyldimethylamine is isolated (25 g, Yield: 83%, purity 98%) by filtration.

Characterization Data:
$^1$H-NMR (DMSO): 9.25(1H, s), 7.05(1H, t), 6.60(3H, m), 3.08(1H, q), 2.05(6H, s), 1.19(3H, d)
13C-NMR (DMSO): 158.0, 146.7, 129.8, 118.7, 114.8, 114.5, 65.8, 43.6, 20.9.
Mass (Methanol): 166.2 (M+1)

Example 2

Preparation of α-m-hydroxy phenylethyldimethylamine

N-methylation was carried out on α-m-hydroxy phenylethylmethylamine (25 g) with Paraformaldehyde (15 g) in presence of Raney Nickel (30 g) in methanol (500 ml) at 80° C. and 10 kg/cm$^2$ of hydrogen pressure in an autoclave. After 3-4 hours the product was isolated by removing Raney nickel and concentrating the filtrate. The product was further purified by dissolving the crude product in Toluene (50 ml) and is crystallized by slow addition of Petroleum ether (150 ml). Pure α-m-hydroxy phenylethyldimethylamine is isolated (23 g, Yield: 85%, purity 98%) by filtration.

Characterization Data:
$^1$H-NMR (DMSO): 9.25(1H, s), 7.05(1H, t), 6.60(3H, m), 3.08(1H, q), 2.05(6H, s), 1.19(3H, d)
13C-NMR (DMSO): 158.0, 146.7, 129.8, 118.7, 114.8, 114.5, 65.8, 43.6, 20.9.
Mass (Methanol): 166.2 (M+1)

Example 3

Preparation of dl-α-m-Hydroxyphenylethylmethylamine

A solution of 33% Methyl amine in Ethanol (170 ml) and 3-hydroxy acetophenone (25.0 g) in Methanol (1000 ml) was charged to an autoclave. To the above solution Raney Ni (2.5 g) was added and the mixture was hydrogenated at 40-80° C. for 8-16 hrs. After the completion of the reaction, the reaction mixture was passed through celite bed and then the solvent was distilled out under vacuum. Cyclohexane was added to the residue and then stirred for 15-30 min. at ambient temperature. The solid material was filtered and dried in hot air oven at 50-60° C. for 5-6 hrs. (Yield 18-25 g).

Example 4

Preparation of α-m-hydroxy phenylethyldimethylamine

N-methylation was carried out on α-m-hydroxy phenylethylmethylamine (25 g) with Paraformaldehyde (15 g) in presence of Raney Nickel (30 g) in methanol (500 ml) at 80° C. and 10 kg/cm$^2$ of hydrogen pressure in an autoclave. After 3-4 hours the product was isolated by removing Raney nickel and concentrating the filtrate. The product was further purified by dissolving the crude product in Toluene (50 ml) and is crystallized by slow addition of Petroleum ether (150 ml). Pure α-m-hydroxy phenylethyldimethylamine is isolated (23 g, Yield: 85%, purity 98%) by filtration.

Characterization Data:
$^1$H-NMR (DMSO): 9.25(1H, s), 7.05(1H, t), 6.60(3H, m), 3.08(1H, q), 2.05(6H, s), 1.19(3H, d)
13C-NMR (DMSO): 158.0, 146.7, 129.8, 118.7, 114.8, 114.5, 65.8, 43.6, 20.9.
Mass (Methanol): 166.2 (M+1)

Example 5

Resolution of dl-α-m-Hydroxyphenylethylmethylamine

Racemic dl-α-m-Hydroxyphenylethylmethylamine (20 g) dissolved in Ethanol (300 ml) was added d-camphorsulphonic acid (33 g), and the reaction mixture was heated to 40-80° C. for 10-60 mins, and then Ethanol was distilled out completely under vacuum, the same operation was repeated twice with Ethanol (100 ml×2). Residual mass was added Ethyl acetate (250 ml) and distilled out. The residual mass was added i-Propanol (60 ml) and stirred for 2-3 days at 0-25° C. The precipitated solid was filtered (10-20 g).

The camphorsulfonate thus obtained was dissolved in Sod. Carbonate soln and then extracted with Ethyl acetate (2×25 ml). Combined organic layer was distilled out and Cyclohexane (50 ml) was added to the residual mass and stirred for 10-30 mins. The solid material was then filtered and dried under vacuum at 40-80° C. (5-10 g) (m.p. 171° C. [α]$_D$ −68.0°; c=5.0 in $C_5H_5N$)

Reference Example 1

Preparation of S-(−)-Rivastigmine 300 ml of tetrahydrofuran (THF) are placed in a 0.51-three-neck flask and sodium hydride as a 60% dispersion in oil (11.3 g) is added slowly under inert conditions (Ar or $N_2$) and stirring. A suspension develops, to which α-m-hydroxy phenylethyldimethylamine (46.5 g, 0.281 mol) is added at room temperature. A solution of the phenolate forms, to which 35.7 g (0.281 mol) of carbamoylchloride are added dropwise over 10 minutes while slightly cooling down to 15° C. The reaction is slightly exothermic. The rate of dropping is kept such that the temperature of the reaction mixture does not exceed 30° C. After all the agent is added, the cooling system is put aside and the reaction mixture is mixed for 2 hours at room temperature. Thereafter, THF is evaporated in a rotary vacuum evaporator. The evaporation residue is partitioned between 200 ml 1N NaOH and 500 ml of ether. The organic layer is separated and the aqueous fraction is shaken with additional 2×200 ml of ether. The combined ether layers are shaken out with 1×100 ml water and 1×50 ml brine. The organic fraction is dried over anhydrous sodium sulfate. The solvent is evaporated and the crude product is vacuum distilled.

b.p.=135-140° C. at 13 Pa 45.6 g of a colorless viscous oil are obtained, i.e. a 80.5% yield. Content GC 99.6%

Reference Example 2

Preparation of Rivastigmine Hydrogentartrate 45.6 g of S-(−)-rivastigmine and 27.4 g of L-(+)-tartaric acid are dissolved in 125 ml of anhydrous ethanol at 60-70° C. under stirring. At this temperature, 630 ml of ethylacetate are gradually added to the solution. The solution is left to cool down to room temperature and to crystallize at +5° C. for at least 12 hours. The precipitated white crystalline product is sucked off, washed with 100 ml of ethylacetate, and vacuum dried at 40° C. 67.5 g of the desired product with m.p.=125-126° C. (i.e. 92.6% of the theoretical yield). ($[a]_D$=+5.5; c=5, ethanol).

While the present invention has been described in terms of its specific embodiments, certain modifications and equivalents will be apparent to those skilled in the art and are intended to be included within the scope of the present invention.

We claim:

1. A process for the preparation of Rivastigmine of formula (I) or pharmaceutically acceptable salts thereof, comprising:
   (a) N-methylation of a compound of formula (III), wherein $R_1=R_2=H$ or $R_1=H$ and $R_2=CH_3$ or an acid addition salt thereof, using paraformaldehyde in the presence of Raney Nickel and hydrogen in a suitable solvent to obtain a compound of formula (II)

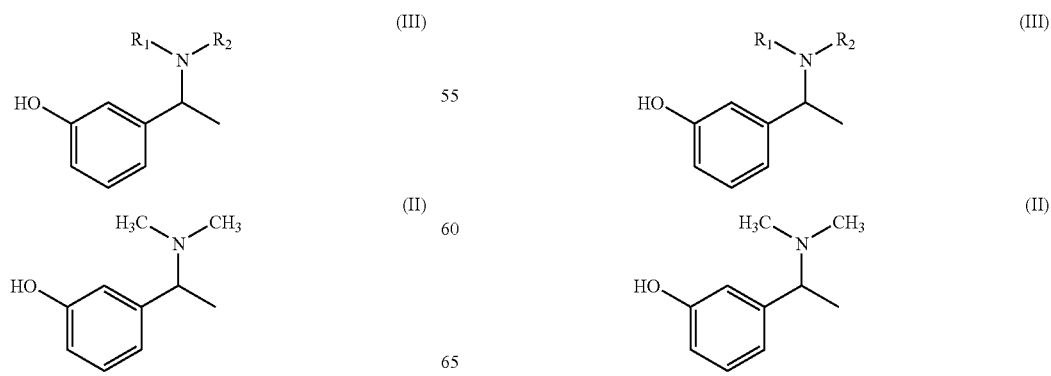

(b) optically resolving the compound of formula (II) to obtain a desired isomer (II')

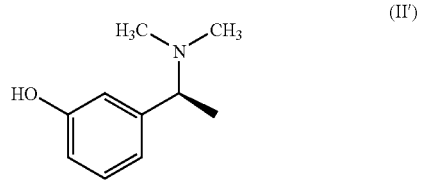

(c) converting the compound of formula (II') to Rivastigmine of formula (I) and optionally converting it to pharmaceutically acceptable salts thereof

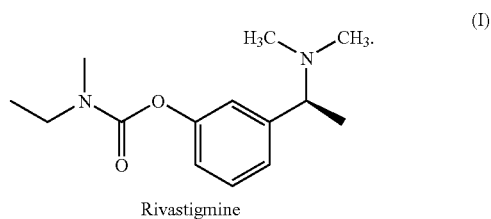

Rivastigmine

2. The process as claimed in claim 1, wherein the suitable solvent is selected from group comprising of alcohols, esters, chlorinated hydrocarbons or mixtures thereof.

3. The process as claimed in claim 2, wherein said suitable solvent is selected from group comprising of methanol, ethanol, isopropanol, ethylacetate, methylacetate, butylacetate, chloroform, methylene dichloride, ethylene dichloride or mixtures thereof.

4. The process as claimed in claim 1, wherein the reaction is carried out at hydrogen pressure maintained between 5 $kg/cm^2$ and 15 $kg/cm^2$.

5. The process as claimed in claim 1, wherein said resolution in step (b) is carried out using d-camphorsulphonic acid.

6. A process for the preparation of Rivastigmine of formula (I) or pharmaceutically acceptable salts thereof, comprising a step of N-methylation of a compound of formula (III), wherein $R_1=R_2=H$ or $R_1=H$ and $R_2=CH_3$ or an acid addition salt thereof, using paraformaldehyde in the presence of Raney Nickel and hydrogen in a suitable solvent to obtain a compound of formula (II) and thereafter converting the compound of formula (II) to Rivastigmine of formula (I)

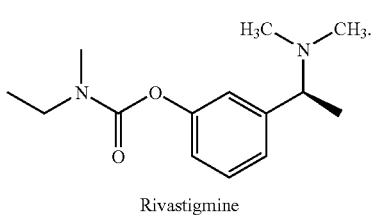

Rivastigmine

7. A process for preparation of a compound of formula (II) comprising: N-methylation of a compound of formula (III), wherein $R_1=R_2=H$ or $R_1=H$ and $R_2=CH_3$ or an acid addition salt thereof, using paraformaldehyde in the presence of Raney Nickel and hydrogen in a suitable solvent to obtain compound of the formula (II)

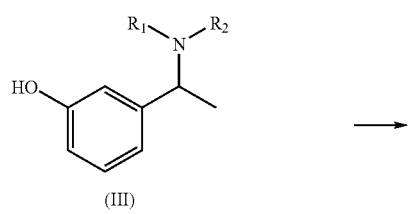

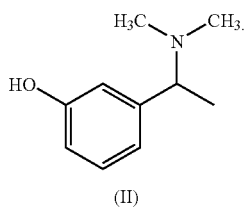

8. The process as claimed in claim 6, wherein the suitable solvent is selected from group comprising of alcohols, esters, chlorinated hydrocarbons or mixtures thereof.

9. The process as claimed in claim 7, wherein said suitable solvent is selected from group comprising of methanol, ethanol, isopropanol, ethylacetate, methylacetate, butylacetate, chloroform, methylene dichioride, ethylene dichioride or mixtures thereof.

10. The process as claimed in claims 7, wherein the suitable solvent is selected from group comprising of alcohols, esters, chlorinated hydrocarbons or mixtures thereof.

* * * * *